United States Patent [19]
Beran et al.

[11] Patent Number: 5,906,204
[45] Date of Patent: May 25, 1999

[54] ENDOTRACHEAL PRESSURE MONITORING AND MEDICATION SYSTEM

[75] Inventors: Anthony V. Beran, Santa Ana; Gordon Shigezawa, Irvine; Mark V. Beran, Santa Ana, all of Calif.

[73] Assignee: Respiratory Support Products, Inc., Irvine, Calif.

[21] Appl. No.: 08/770,014

[22] Filed: Dec. 19, 1996

[51] Int. Cl.⁶ .................................................. A61M 16/10
[52] U.S. Cl. ...................... 128/207.14; 128/912; 600/529
[58] Field of Search ........................ 128/207.14, 202.27, 128/204.21, 207.15, 911, 912; 600/529

[56] References Cited

U.S. PATENT DOCUMENTS

| | | | |
|---|---|---|---|
| 4,681,100 | 7/1987 | Brychta et al. | 128/207.14 |
| 4,723,543 | 2/1988 | Beran | 128/207.14 |
| 4,796,615 | 1/1989 | Bullock et al. | 128/202.27 |
| 4,815,459 | 3/1989 | Beran | 128/207.14 |
| 4,821,709 | 4/1989 | Jensen | 128/204.21 |
| 5,065,754 | 11/1991 | Jensen | 128/207.14 |
| 5,101,817 | 4/1992 | Etter | 128/207.14 |
| 5,207,220 | 5/1993 | Long | 128/207.14 |
| 5,431,157 | 7/1995 | Mourkidou et al. | 128/207.14 |
| 5,462,061 | 10/1995 | Malouvier et al. | 128/204.17 |
| 5,492,109 | 2/1996 | Hirschl et al. | 128/207.14 |
| 5,499,625 | 3/1996 | Frass et al. | 128/207.14 |
| 5,509,408 | 4/1996 | Kurtis | 128/207.14 |
| 5,546,935 | 8/1996 | Champeau | 128/207.14 |
| 5,588,424 | 12/1996 | Insler et al. | 128/207.14 |

FOREIGN PATENT DOCUMENTS

| | | |
|---|---|---|
| 552916 | 7/1993 | European Pat. Off. . |
| 1441391 | 1/1969 | Germany . |
| 29715521 | 1/1998 | Germany . |
| 9317744 | 9/1993 | WIPO . |

*Primary Examiner*—John G. Weiss
*Assistant Examiner*—V. Srivastava
*Attorney, Agent, or Firm*—Price,Gess & Ubell

[57] ABSTRACT

An endotracheal pressure monitoring and medication system includes an endotracheal tube having a primary lumen and a secondary lumen with a connector having an outside diameter configured to provide a frictional fit with a Y-tube and a tubular conduit with an outside diameter providing a frictional fit with a proximal end of the endotracheal tube. The connector includes a passageway extending from the tubular conduit to a fitting whereby medication can be applied or pressure can be monitored. A sleeve member extends about on a seal to the endotracheal tube with a cantilevered branch tube providing fluid communication with the secondary lumen. The cantilevered branch tube can be connected to a flexible tube member to enable either the application of medication or the monitoring of pressure. A pressure monitor is capable of measuring the pressure from either the opening of the secondary lumen in the trachea of the patient and/or the connector whereby gases can be sampled and pressure can be individually monitored or differentially monitored to provide a pneumotach measurement at an optimum location relative to the patient's airways.

12 Claims, 3 Drawing Sheets

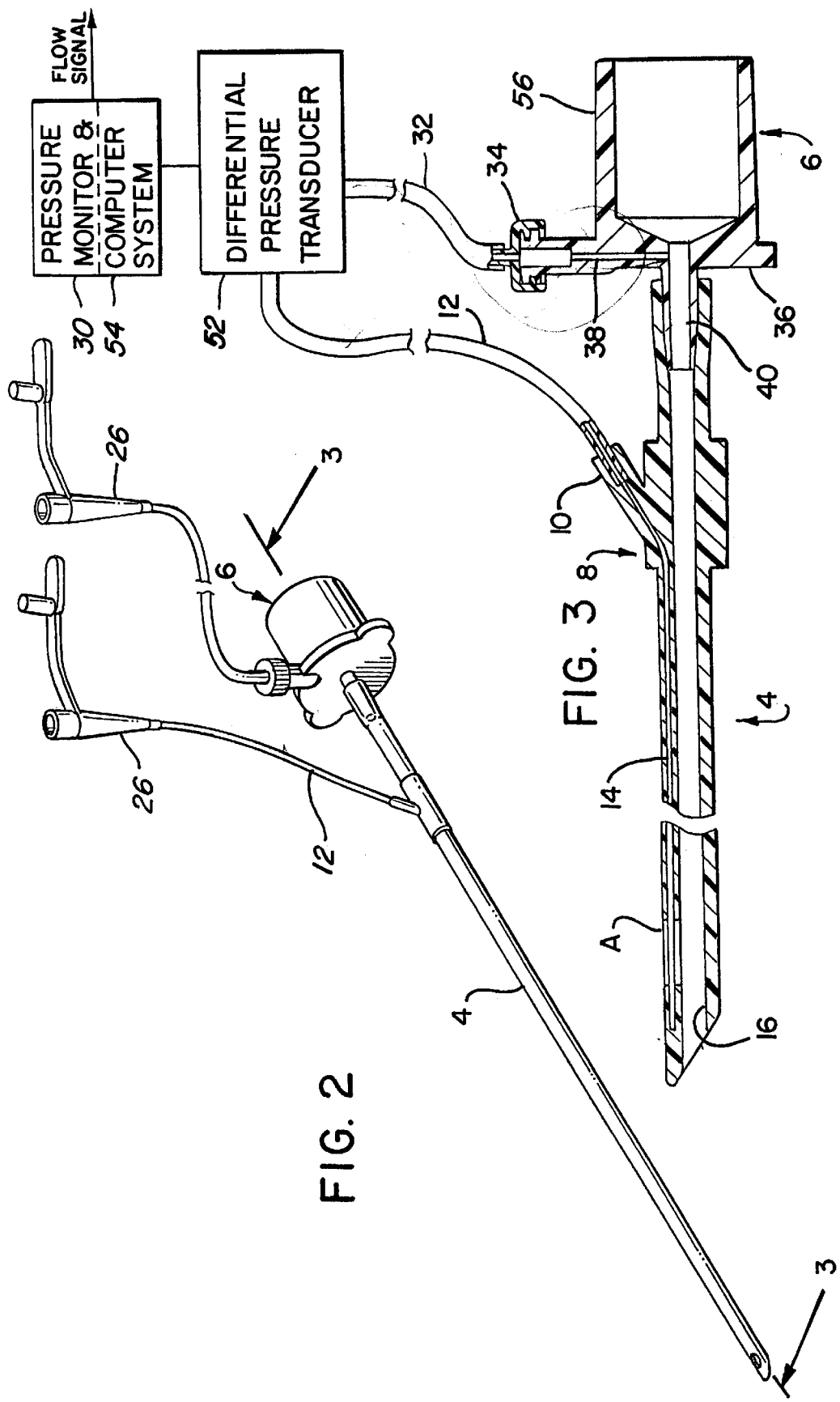

ENDOTRACHEAL PRESSURE MONITORING AND MEDICATION SYSTEM

BACKGROUND OF THE INVENTION

1. Field of the Invention

The present invention is directed to a combination endotracheal tube and connector and, more particularly, to such a combination that would enable both an endotracheal pressure monitoring and medication system which permits continued monitoring of patient pressure at an advantageous position during the application of a medication or, alternatively, permits a simultaneous application of two separate medications.

2. Description of Related Art

Ventilators are commonly employed to assist a patient in breathing and include two main lines which are independently connected from the ventilator to separate branched arms from a Y-tube junction. An adapter is inserted into the open stem of the Y-tube for further connection with an endotracheal tube extending from the trachea of a patient. It is often important to measure the respiratory pressure of inhaled gas and the respiratory flow of the patient, along with measuring the composition of the exhaled gas.

Additionally, medicinal drugs can also be introduced to the patient's lungs through an intubated endotracheal tube. This can be accomplished by injecting a pharmacological agent or therapeutic drug into the proximal end of the endotracheal tube and then pressurizing the drug down the tube into the lungs. An example of a drug delivering endotracheal tube is disclosed in U.S. Pat. No. 5,540,224.

An endotracheal tube connector which minimizes any dead space in the respiratory system, which can be a health hazard for very small patients such as newborn babies and discloses a pneumotach, is disclosed in U.S. Pat. No. 4,723,543.

As is known, special problems can occur in newborn and pediatric applications of ventilators, and the measurements of airway pressure is important because lungs ventilated with insufficient pressure will produce insufficient $O_2$ and $CO_2$ exchange. The application of an excessive pressure, however, can produce decrease pulmonary venus return, which lowers cardiac output and/or causes pneumothorax. Thus, attempts to achieve an accurate measurement of airway pressure is important. As can be appreciated, in a ventilator conduit, the dynamic pressure can change at different points along the conduit. These changes in pressure depend on many different variables such as the compliance of the conduit segment, radius of conduit at the pressure measurement site, frequency of the dynamic pressure changes, leaks, constrictions, etc. The intra-alveolar pressure affects $O_2$ and $CO_2$ exchange, and if the pressure is too high, it can decrease cardiac output and cause pneumothorax. Under routine clinical conditions, direct measurement of dynamic intra-alveolar pressure is generally not feasible. Conventionally, this measurement is taken at a site which is a compromise and is usually measured adjacent the proximal end of the endotracheal tube or at a connector mounting the tube.

Thus, the prior art is still seeking improvements in both the measurement of pressure and in the application of medicinal fluid to a patient who is being subjected to respiratory-assisted breathing.

OBJECTS AND SUMMARY OF THE INVENTION

The present invention is directed to a combination endotracheal tube and connector assembly, with the endotracheal tube having a primary lumen to enable patient ventilation with a ventilator, and a secondary lumen extending substantially adjacent the primary lumen for a substantial length of the primary lumen with an opening at the distal portion of the endotracheal tube. A sleeve member may be integrally formed with the endotracheal tube or separately fixed to the tube to extend about and be sealed to a proximal portion of the endotracheal tube with a cantilevered branch tube providing fluid communication with the secondary lumen. A flexible tube member can be connected to the branch tube at one end, and can have a receptacle at the other end of a configuration to receive a first source of medication. A connector with a cylindrical connector collar having an outside diameter configured to provide a frictional fit with a Y-tube and an internal tubular conduit with an outside diameter providing a frictional fit with a proximal end of the endotracheal tube is provided. The connector includes a passageway extending from the tubular conduit to a fitting wherein a source of a second medication can be applied through the fitting. A pressure monitor can also be connected to the flexible tube member to enable monitoring of patient ventilation pressure adjacent the inserted distal end of the endotracheal tube through the secondary lumen passageway. As can be appreciated, a continued monitoring of patient ventilation pressure can occur while medication is also being simultaneously applied to the patient. Alternatively, a differential pressure measurement can be made between the connector tube and the distal end of the endotracheal tube.

BRIEF DESCRIPTION OF THE DRAWINGS

The objects and features of the present invention, which are believed to be novel, are set forth with particularity in the appended claims. The present invention, both as to its organization and manner of operation, together with further objects and advantages, may best be understood by reference to the following description, taken in connection with the accompanying drawings.

FIG. 2 is a perspective view of the endotracheal tube and connector member;

FIG. 3 is a cross-sectional view of the endotracheal tube and connector member.

DETAILED DESCRIPTION OF THE PREFERRED EMBODIMENTS

The following description is provided to enable any person skilled in the art to make and use the invention and sets forth the best modes contemplated by the inventors of carrying out their invention. Various modifications, however, will remain readily apparent to those skilled in the art, since the general principles of the present invention have been defined herein specifically to provide an endotracheal pressure monitoring and medication system.

Figure 1:
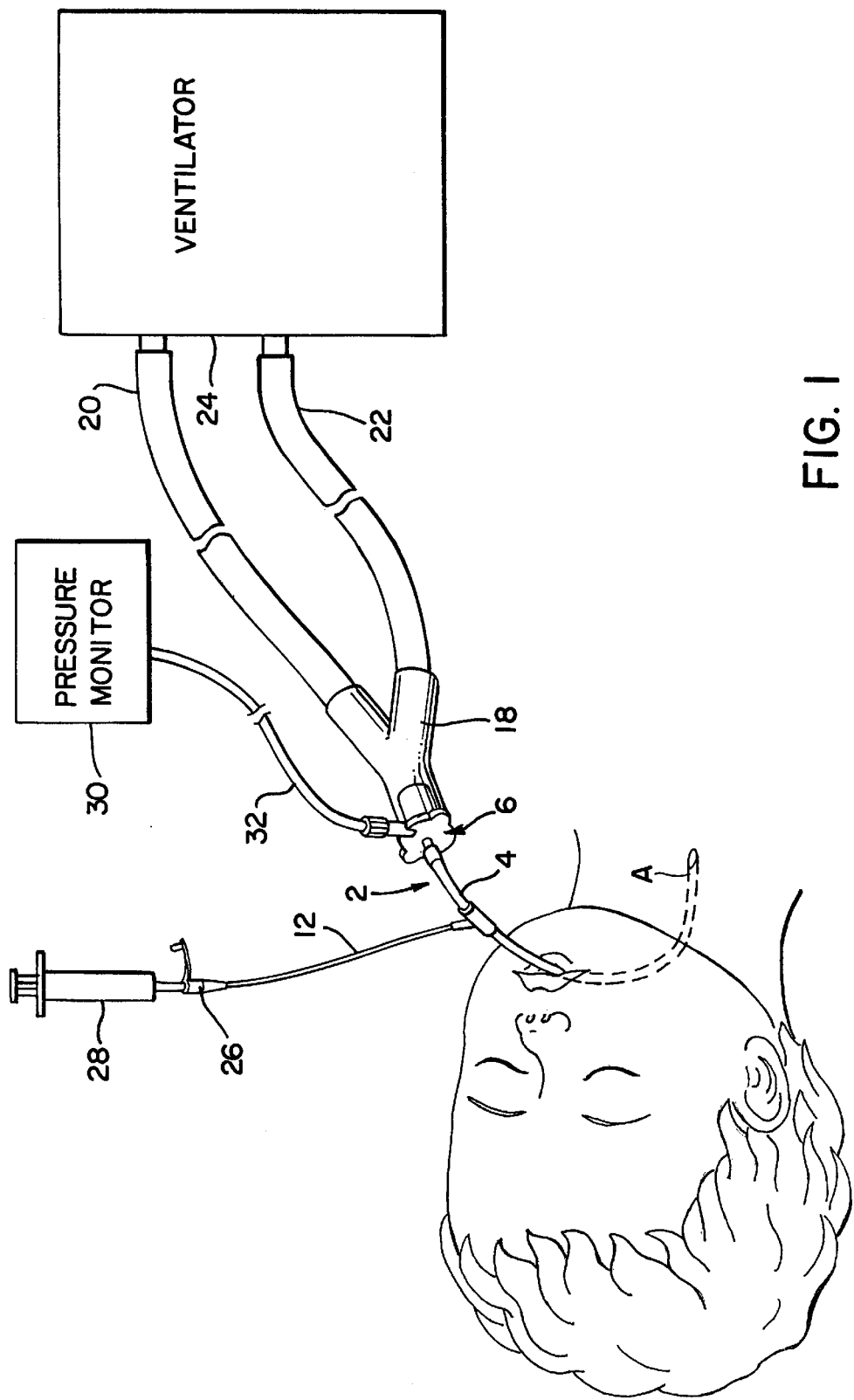
FIG. 1 is a perspective view of the application of the endotracheal tube and connector of the present invention for providing a pressure monitoring system while permitting the application of medication to the patient.

Referring to FIG. 1, an endotracheal pressure monitoring and medication system is disclosed in a pediatric environment with an appropriately-sized endotracheal tube and connector assembly 2 being chosen in sizes appropriate to the anatomical and physiological requirements of the pediatric patient. For example, a pediatric internal diameter I.D. could be in the range of 2.5 to 5.0 mm. For an adult application, the internal diameter, I.D., could be in the range of 5.0 to 10.0 mm. The endotracheal tube 4 is sealingly connected to the connector 6 at a proximal end with the distal end inserted into the patient. For example, a 3.0-mm I.D. with a 4.2-mm O.D. is appropriately connected to a 3.0-mm connector 6. The endotracheal tube 4 as seen in FIG. 3 has a branched junction 8 adjacent the proximal end of the endotracheal tube 4 which includes a flexible cantilevered adapter 10. The adapter 10 has an enlarged internal aperture to complement the O.D. of a flexible tube 12. The flexible tube 12 can abut against a flange or shoulder 50 that extends around the entrance port to a secondary lumen 14. (See FIG. 4.) The flexible tube 12 can be sealingly connected to the cantilevered adapter 10 with the flexible tube 12 having the same internal I.D. as the secondary lumen 14. For example, the I.D. of the secondary lumen can be 0.3 mm. As can be seen, the secondary lumen 14 extends approximately the same length as the primary lumen 16.

The pressure drops along a ventilator conduit are generally influenced by the radius of the inside I.D. of the conduit and, to a lesser extent, by the influence of its length. This is important in determining where the airway pressure should be measured. As can be seen, the ventilator conduit also includes a Y-connector 18 that is respectively connected to an inhalation tube 20 and an exhalation tube 22 that are, in turn, connected to the ventilator 24. Since the ventilator conduit comprises many different inside diameters of materials at different compliances, the dynamic pressures will change at different points along the conduit. These changes in pressure depend on many different variables such as compliance of the conduit segment, radius of conduit at the pressure measurement site, frequency of the dynamic pressure changes, leaks, constrictions, etc. By providing a location to measure the pressure closest to the patient's upper airways or in the trachea, a more accurate measurement can be achieved.

In FIG. 1, the situs of pressure measurement is considered secondary to the application of medication simultaneously through the flexible tube 12. The flexible tube 12 terminates in a receptacle 26 adapted to sealingly fit a syringe applicator 28. Thus, medication is accordingly applied through the secondary lumen 14. Pressure monitoring can be simultaneously accomplished with a pressure monitor 30 connected through a pressure conduit 32 to a fitting 34 mounted on the flange 36 of the coupler 6. A conduit 38 of approximately the same I.D. as the secondary lumen 14 is connected to the tubular conduit 40 of the connector 6. The tubular conduit 40 has an exterior outer diameter slightly greater than the inner diameter of the endotracheal tube and an inner diameter approximately the size of the inner diameter of the primary lumen 16 of the endotracheal tube. As can be seen, the pressure monitor 30 is measuring at a situs in the endotracheal connector 6 where the I.D. is equivalent to the I.D. of the endotracheal tube 4.

The combination of the endotracheal tube and connector assembly 2 can be conveniently packaged as a sterile unit for hospital use. The primary lumen 16 and secondary lumen 14 can be formed in a molded or extruded plasticized polyvinyl chloride, polyurethane, or silane. The primary lumen 16 has a larger diameter than the secondary lumen 14. The secondary lumen 14 extends substantially parallel along a substantial portion of the length of the primary lumen 16. The connector 6 is molded from a plastic as a relatively rigid component with an integral collar 56 having an outside diameter configured to provide a frictional fit with a Y-tube 18 of a ventilator system and a tubular conduit 40 that can be permanently affixed by adhesives to the endotracheal tube. A secondary lumen connector 8 in the form of an enlarged portion or sleeve 8 of the endotracheal tube is provided with a cantilevered branch tube extending at approximately 30 degrees from the surface of the endotracheal tube.

Another aspect of measurement is determining the components of both the inspiratory and expiratory gases. Again, the measurement of these gases depends on the point in the ventilator circuit where the gases are sampled. Gases flowing in a large conduit exhibit concentration profiles within the conduit similar to a pressure profile. The gas concentration along the wall of the conduit approximates the mean or average concentrations. The dynamically changing concentrations are more evident near the center of the conduit. By measuring gas concentration at an I.D. equivalent to the I.D. of the endotracheal tube, the gas flow in this location is probably turbulent and the concentration profile does not exist. As a result, a more precise measurement of the inspiratory and expiratory gas concentrations can be achieved. In the embodiment shown in FIG. 1, the application of the medication through the medicinal applicator or syringe 28 is given first priority and occupies the use of the secondary lumen 14 of the endotracheal tube 4, while the pressure monitoring 30 is accomplished through the connection of the pressure tube 32 to the fitting 34 on the connector flange 36. The fitting 34 can be a Luer lock fitting. If it is desired to take the measurement within the trachea of the patient such as at point A, the pressure monitor could be connected to the flexible tube 12.

As seen in FIG. 3, if it is desired to take a measurement of respiratory flow, it would be possible to measure the change in pressure of the gas as it flows between point A and the conduit 38 to, in effect, provide a pneumotach with the length of the primary lumen 16 between these two points providing an appropriate restriction to fluid flow. As can be appreciated, flow sensitivity will increase as the primary lumen 16 I.D. decreases. A differential pressure transducer 52 of a known type can be appropriately connected to the tubes 12 and 32 to generate a differentiated pressure signal. To compensate for any nonlinearity in such measurements, a table of values corresponding to flow rates per specific tube size can be generated and stored, for example, in the RAM of a computer system 54, which also receives the differential pressure signal. The measurements of the pressure for each position can be coordinated with a set of values in the table to provide a Δ pressure drop equivalent to the respiratory flow. Measurements such as this will permit an optimum ventilator adjustment for the patient.

Figure 4:
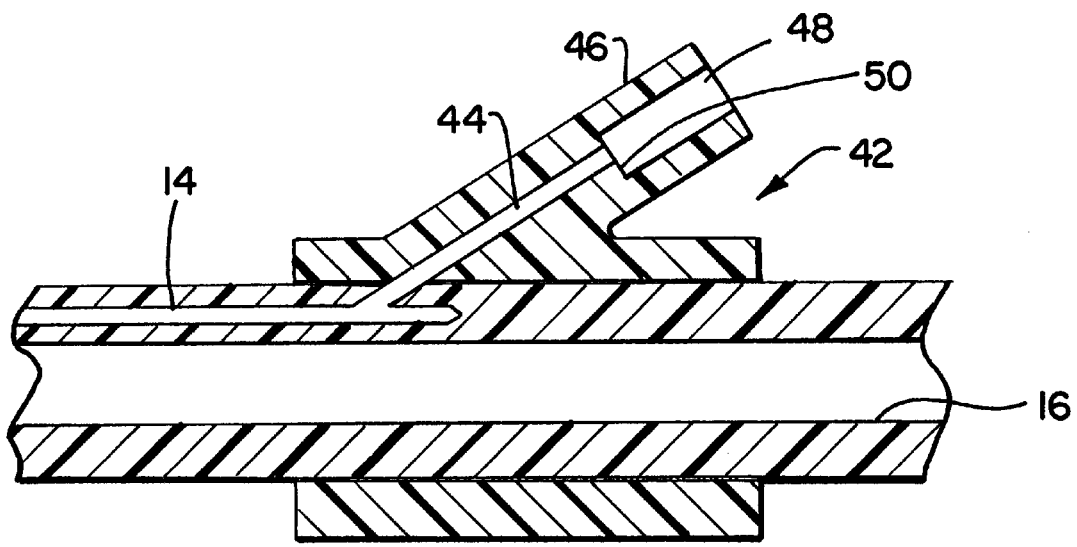
FIG. 4 is a cross-sectional view of an alternative endotracheal sleeve branch tube.

In summary, the combination of an endotracheal tube 4 with a connector 6 as shown in the perspective view of FIG. 2 can enable the application of a superior endotracheal pressure monitoring and medication delivery system. In the embodiment of FIG. 2 the branch junction or secondary lumen connector 8 can be a separate cylindrical sleeve 42 as shown in FIG. 4, which is adhered by an adhesive to weld it about the outer perimeter of the endotracheal tube. The wall of the endotracheal tube is pierced to facilitate a communication with a conduit 44. Preferably, a polyvinylchloride plastic is used to provide sufficient flexibility for connection with a flexible tube such as the flexible tube 12 shown in FIG. 3. The flexible tube or conduit 12 can be inserted within a cantilevered flexible adapter 46 having an enlarged opening 48 with a circular flat ledge or flange seat 50 for receiving the end of the flexible tube 12. Again, an appropriate adhesive can be used to seal the flexible tube 12 to the flexible adapter 46.

It is not intended to limit this invention to the particular embodiments disclosed but, on the contrary, the invention is to cover all modifications and alternative constructions all within the spirit and scope of the invention as expressed in the appended claims and as known by those skilled in the field as equivalents to the elements set forth in the claims.

What is claimed is:

1. An endotracheal pressure monitoring system comprising:

an endotracheal tube having a primary lumen and a smaller secondary lumen, the secondary lumen extending substantially parallel along a substantial portion of the length of the primary lumen from a distal end of the endotracheal tube to be inserted into a patient to a proximal end exterior of the patient, the primary lumen and the secondary lumen are both open adjacent the distal end to provide fluidic communication with a trachea of the patent;

a fluidic pressure monitor; and a conduit member connected to a proximal end of the secondary lumen and to the fluidic pressure monitor to transmit the fluidic pressure in the secondary lumen to the pressure monitor, whereby the primary lumen can provide ventilation to a patient and the secondary lumen is open at the distal end of the endotracheal tube to enable direct fluidic monitoring of patient ventilation pressures adjacent the inserted distal end of the endotracheal tube.

2. The invention of claim 1 further including a sleeve member with a cantilevered branch tube mounted around the endotracheal tube and fluidly connected to the secondary lumen and the conduit member mounted in the branch tube.

3. The invention of claim 2 wherein the sleeve member is integrally formed with the endotracheal tube.

4. The invention of claim 1 further including a connector with a cylindrical connector collar having an outside diameter configured to provide a frictional fit with a Y-connector and a tubular conduit with an outside diameter providing a frictional fit with a proximal end of the endotracheal tube, the connector having a passageway which communicates with the tubular conduit, and means for connecting the passageway with the fluid pressure monitor to enable a measurement of differential pressure between the primary and secondary lumens.

5. The invention of claim 1 further including a connector having a passageway which communicates with the primary lumen and a flexible tube member connected to the passageway and having a receptacle at the other end of a configuration to receive a fluid medication for delivery to the patient via the primary lumen while pressure is measured via the secondary lumen.

6. A combination endotracheal tube and connector comprising:

an endotracheal tube having a primary lumen to enable patient ventilation with a ventilator and a secondary lumen extending substantially adjacent the primary lumen for a substantial length of the primary lumen;

a sleeve member extending about and sealed to the endotracheal tube with a cantilevered branch tube providing fluid communication with the secondary lumen;

a flexible tube member connected to the branch tube at one end and having a receptacle at the other end of a configuration to receive a first medication; and a connector with a cylindrical connector collar having an outside diameter configured to provide a frictional fit with a Y-tube and a tubular conduit with an outside diameter providing a frictional fit with a proximal end of the endotracheal tube, the connector including a passageway extending from the tubular conduit to a fitting whereby a second medication can be alternatively or simultaneously applied through the fitting.

7. The invention of claim 6 further including a second flexible tube member connected to the fitting at one end and having a receptacle at the other end of a configuration to receive a second medication.

8. An endotracheal pneumotach system for measuring gas flow in a patient comprising:

an endotracheal tube having a primary lumen and a smaller secondary lumen, the secondary lumen extending substantially parallel along a substantial portion of the length of the primary lumen from a distal end of the endotracheal tube to be inserted into a patient to a proximal end exterior of the patient, the primary lumen and the secondary lumen are both open adjacent the distal end to provide fluidic communication with a trachea of the patient;

a connector member connected to the proximal end of the primary lumen, a passageway through the connector member communicating with the primary lumen;

a differential pressure transducer for providing a differential pressure signal between a pressure in the primary lumen and a pressure in the secondary lumen;

first means for connecting the secondary lumen adjacent the proximal end to the differential pressure transducer;

second means for connecting the passageway to the differential pressure transducer; and means connected to the differential pressure transducer for processing the differential pressure signal existing between the distal open end of the secondary lumen and connector member communicating with the primary lumen and providing a measurement of a gas flow rate.

9. The invention of claim 8 wherein the first means includes a sleeve member with a flexible adaptor and a conduit, the conduit being attached to the adaptor and the pressure transducer.

10. The invention of claim 8 wherein the means for processing includes a computer unit with a stored set of values representing flow rates per size of endotracheal tubes for correlating a differential pressure signal with a gas flow rate.

11. A combination endotracheal tube and connector assembly comprising:

a flexible endotracheal tube having a primary lumen and a secondary lumen, the primary lumen having a larger cross-sectional area than the secondary lumen, the secondary lumen extending substantially parallel along a substantial portion of the length of the primary lumen from a distal end of the endotracheal tube to be inserted into a patient to a proximal end, exterior of the patient, the primary lumen and the secondary lumen are both open at the distal end to provide fluidic communication with the patient;

a connector with a cylindrical connector collar having an outside diameter configured to provide a frictional fit with a Y-tube and a tubular conduit with an outside diameter affixed to one end of the primary lumen and having an inside diameter of approximately the same diameter as an inside diameter of the primary lumen, the connector including a passageway extending from the tubular conduit to a fitting whereby fluid egress can be provided to the primary lumen;

a secondary lumen connector positioned on the endotracheal tube adjacent the connector and including a flexible cantilevered branch tube extending from the endotracheal tube and providing fluid egress to the secondary lumen; and a flexible tube affixed in the cantilevered branch tube for accessing the secondary lumen.

12. The invention of claim 11 wherein the secondary lumen connector is integrally formed to extend around the endotracheal tube.

* * * * *